United States Patent
Maddess

[11] Patent Number: 5,912,723
[45] Date of Patent: Jun. 15, 1999

[54] METHOD AND APPARATUS FOR EARLY DETECTION OF GLAUCOMA

[75] Inventor: Teddy Lee Maddess, Kaleen, Australia

[73] Assignee: Australian National University of Acton, Acton, Australia

[21] Appl. No.: 08/732,430
[22] PCT Filed: Apr. 28, 1995
[86] PCT No.: PCT/AU95/00252
  § 371 Date: Feb. 18, 1997
  § 102(e) Date: Feb. 18, 1997
[87] PCT Pub. No.: WO95/29627
  PCT Pub. Date: Nov. 9, 1995

[30] Foreign Application Priority Data

Apr. 29, 1994 [AU] Australia ............... PM 5379

[51] Int. Cl.⁶ .................................................. A61B 3/00
[52] U.S. Cl. ...................... 351/246; 351/211; 351/221
[58] Field of Search ................................. 351/246, 205, 351/211, 221, 224, 237, 243, 239; 128/745

[56] References Cited

U.S. PATENT DOCUMENTS

| | | | |
|---|---|---|---|
| 3,910,690 | 10/1975 | Regan | 351/205 |
| 4,634,243 | 1/1987 | Massof et al. | 351/243 |
| 4,822,162 | 4/1989 | Richardson et al. | 351/243 |
| 5,176,147 | 1/1993 | Bodis-Wollner | 351/239 |
| 5,539,482 | 7/1996 | James et al. | 351/246 |

FOREIGN PATENT DOCUMENTS

| | | |
|---|---|---|
| 40241/89 | 3/1990 | Australia . |
| 33864/93 | 9/1993 | Australia . |
| WO 95/08290 | 3/1995 | WIPO . |

OTHER PUBLICATIONS

Patent Abstracts of Japan, C–1135, p. 44, JP,A,5–207975 (Nidek Co. Ltd.) Aug. 20, 1993.

*Primary Examiner*—Huy Mai
*Attorney, Agent, or Firm*—Townsend and Townsend and Crew; Guy W. Chambers

[57] ABSTRACT

A diagnostic test for glaucoma which preferably uses four types of frequency doubled illusion patterns to determine the existence of glaucomatous damage in different regions of the eye. The four frequency doubled illusion patterns are preferably generated on a cathode ray tube by single spatial frequencies in the range of 0.1 to 4.0 cycles per degree whose contrast is modulated in time at between 10 and 50 Hz. As the contrast of each of these patterns is lessened, a threshold value is determined for each pattern at the point where the subject can only discern thick vertical stripes in the test pattern rather than the frequency doubled illusion. By comparing the detected threshold values for the various patterns among themselves and with other test data for normal sighted persons, the presence of glaucomatous damage to different regions of the eye can be detected.

12 Claims, 2 Drawing Sheets

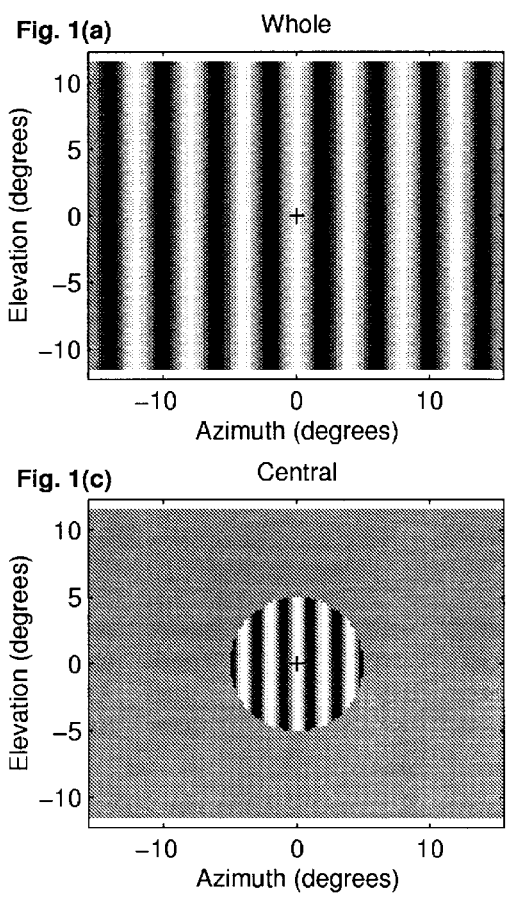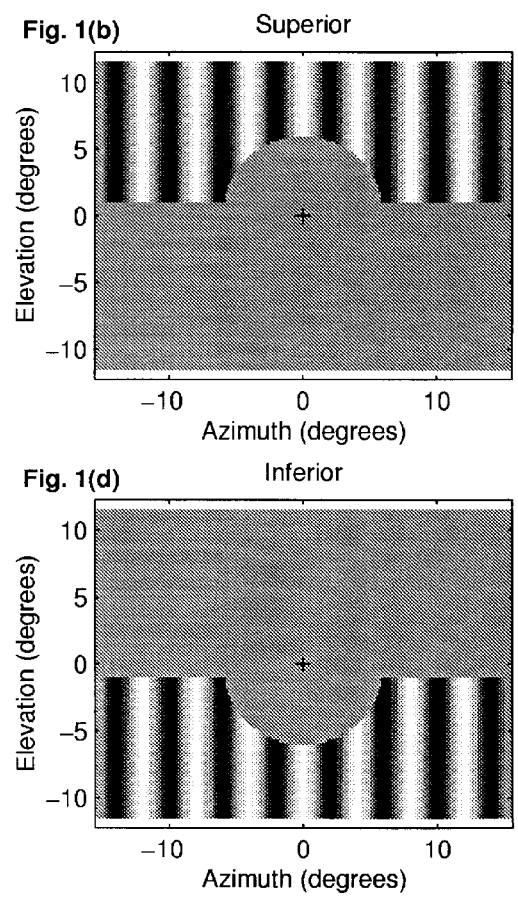

METHOD AND APPARATUS FOR EARLY DETECTION OF GLAUCOMA

TECHNICAL FIELD

This invention concerns the detection of damage to the retina by the eye disease glaucoma. More particularly, it concerns a method and apparatus whereby a person suffering from glaucoma can be diagnosed rapidly and objectively while the disease is in its early stages, thus improving the prospects for successful treatment to reduce the progress of the irreversible blindness characteristic of glaucoma. The invention involves a psycho-physical test of the ability of a subject to observe grating patterns which are presented in different areas or zones of the subject's visual field.

BACKGROUND TO THE INVENTION

In the eye, the final stage of image processing in the retina is performed by retinal ganglion cells. The axons of the ganglion cells project out of the eye to form the optic nerve. Glaucoma, a disease which produces irreversible blindness if not treated early enough, destroys the ganglion cells. Until recently, the typical first sign of the presence of glaucoma has been the loss of a portion of the peripheral visual field, which is referred to as a "scotoma". Unfortunately, by the time a scotoma is detected, the disease has reached a stage where treatment can at best prevent further irreversible blindness.

One approach that has been used to screen subjects for glaucoma at an earlier stage than when a scotoma has developed is to test the intraocular tension of a patient. A symptom of glaucoma is the increase of intraocular tension. Tests of intraocular tension, however, usually involve the use of drugs, are time consuming, and are unpleasant for the subject. Moreover, some glaucoma sufferers do not exhibit intraocular tensions above about 21 mm of mercury (such subjects have what is called "normal-tension glaucoma"). Thus, testing the intraocular tension of a subject is not a reliable method for the early detection of glaucoma.

Another proposal for the early detection of glaucoma has involved the assessment of colour vision defects. Simple tests of colour vision defects, however, have shown a lack of correlation between the defects noted and the presence of optic disc cupping. More complex tests of colour vision defects involving anomaloscopy are too difficult for clinic use. Moreover, those tests cannot differentiate between colour vision defects caused by glaucoma and colour deficits resulting from amblyopia and optic neuritis. In addition, it has been reported that up to 25 per cent of subjects who have a glaucomatous scotoma exhibit no colour deficit. Thus assessment of colour deficits in a person's vision is not a reliable method of detecting glaucoma in its early stages, even if it should become practical to perform detailed colour vision tests clinically.

A conventional method for characterising damage by glaucoma involves perimetry. In a typical perimetric investigation, a series of small luminous dots are projected onto a screen which is placed in front of a subject. The subject's vision is assessed on the basis of whether the subject testifies to seeing each dot as it is presented. This procedure, being a serial search, is very time consuming and is prone to errors arising from a subject's fallibility. Moreover, this perimetric technique cannot be used selectively for assessing glaucomatous damage, for it provides only an indication of localised blind spots in the visual field of a subject, which may arise from a variety of retinal and central nervous system disorders which affect vision. In particular, perimetric investigations take no account of the spatial scale of the visual system, for they typically use dots of the same size in all parts of the visual field, and in no way do they cater to any visual subsystem which may be damaged by glaucoma.

A psycho-physical test for the onset of glaucoma which was developed by the present inventor, and which has been found to be an effective method of detecting the presence of glaucomatous damage at an early stage, is described in the specification of Australian patent No 611,585 and in the specification of the corresponding U.S. Pat. No. 5,065,767. That test involves the presentation of a sinusoidal grating pattern to a subject while the contrast of the pattern is modulated at a frequency in the range from about 10 Hz to about 50 Hz, so that the subject observes a frequency-doubled pattern of the grating. The contrast of the pattern is then reduced until a threshold value is reached, at which value the frequency-doubled pattern is no longer observed by the subject. This threshold value is then compared with the threshold value for persons having normal, healthy vision. A higher than normal threshold value indicates that the subject may be suffering from glaucoma. Persons with well-developed glaucoma have threshold values that are approximately twice the threshold value of a person zenith healthy vision. The pattern is conveniently established on the screen of a cathode ray tube, controlled by a programmed microprocessor.

The test of Australian patent No 611,585 and U.S. Pat. No. 5,065,767, although an effective, non-invasive, quick, and easy to perform test, reveals an average loss of ganglion cells on the retina of a subject due to glaucomatous damage. The loss of ganglion cells in one region of the retina may be masked if the threshold contrast value for the disappearance of the frequency-doubled illusion is only slightly below the average value for persons having healthy vision.

SUMMARY OF THE INVENTION

The prime objective of the present invention is the provision of a rapid, reliable and non-invasive test for retinal damage caused by glaucoma which affects only part of the visual field of a subject. This objective is achieved by presenting to a subject visual stimuli which have a spatial distribution and spatio-temporal structure which are tailored to a visual subsystem that is highly likely to be effected by damage due to glaucoma. The test thus provides a rapid and objective test with high sensitivity and specificity for glaucoma.

Briefly, the present invention involves measuring, for different regions of a subject's field of view, the minimum contrast at which the frequency-doubled illusion of a contrast-modulated grating pattern can be seen by a subject. This "contrast threshold" measurement is repeated as frequency-doubled patterns are presented to a subject in several areas of the subject's field of view.

The normal optical function of the eye is such that each part of the visual field maps onto different parts of the retina. Thus, when patterns which are seen in their frequency-doubled form are presented in different parts of the visual field of a subject, they stimulate the corresponding respective parts of the retina. In this way, different parts of the retina can be tested separately, or together. The spatial layout of the visual stimuli presented to the subject must be such that the stimuli are imaged on different areas or zones of the retina, so that a spatial distribution of damage to vision by glaucoma can be assessed.

In one broad form, the present invention provides a method of assessing the presence of glaucomatous damage to the visual system of a subject, the method comprising steps of:

(a) dividing the visual field of view of said subject into a plurality of zones;

(b) presenting patterns within selected zones, said patterns having spatial and temporal characteristics consistent with observing a spatial frequency doubled illusion;

(c) measuring, preferably between 2 and 5 times, a contrast threshold at which said subject can just discern each pattern while fixating on a fixation spot; and, (d) calculating the mean of the logarithm of the threshold values obtained for each zone to determine the zone which produces the highest threshold, and comparing the maximal threshold with a standard value based on subjects of normal vision.

Preferably, said zones include one or any combination of the entire or a selected portion of the Superior and/or Inferior visual fields wherein the Central visual field is optionally excluded therefrom, the Central visual field, and/or the whole visual field.

Also preferably, the Inferior and/or Superior visual fields are sub-divided into left and right halves about the vertical meridian region, to form four quadrant zones.

Preferably, the threshold values from the four quadrant zones are ranked according to threshold values before analysis.

Most preferably, said fixation spot is located at 0° azimuth and elevation in said visual field.

In a preferred form, the outer extent of the Whole, Inferior and Superior visual fields is extended up to ±30° azimuth and/or elevation.

Preferably, said contrast thresholds are determined by an automated procedure.

Preferably, said patterns comprise sinusoidal grating patterns having generally elongate striations being modulated at a frequency in the range of 10 Hz to 50 Hz.

In a further broad form, the present invention provides an apparatus for assessing the presence of glaucomatous damage to the visual system of a subject, comprising:

a display system adapted to present patterns in a selected plurality of zones dividing the visual field of a subject, said patterns having spatial and temporal characteristics consistent with observing a spatial frequency double illusion; and means to adjust the contrast of said patterns to a contrast threshold at which said subject can just discern each pattern.

Preferably, the contrast adjustment should have a resolution of 10 bits or 1 part in 1024. The contrasts may be presented in logarithmic units with incremental steps of about 0.5 decibels beginning at a lowest contrast of about –44 decibels, that is a minimum contrast of about 0.006.

Preferably, the apparatus further comprises means to calculate the mean of the logarithm of the threshold values to determine the zone which produces the highest threshold; and means to compare said maximal threshold with a standard value based on subjects having normal vision.

Preferably, said displaying system is adapted to present said patterns in a plurality of selected zones dividing the visual field of a subject, including one or any combination of the entire or a selected portion of the Superior and/or Inferior visual fields where the Central visual field is optionally excluded therefrom, the central visual field, and/or the whole visual field.

Also preferably, in said displaying system said patterns comprise sinusoidal grating patterns having generally elongate striations modulated at a frequency in the range of 10 Hz to 50 Hz.

Most preferably, said display system is a cathode ray tube screen.

BRIEF DESCRIPTION OF THE DRAWINGS

The present invention will become more fully understood from the following detailed description of a preferred but non-limiting embodiment thereof, described in connection with the accompanying drawings, wherein:

FIGS. 1(a–d) show four zones of the visual field of view of a subject, FIG. 1(a) displaying the whole field, FIG. 1(b) displaying the Superior Field wherein the Central field is excluded, FIG. 1(c) displaying the Central field, and, FIG. 1(d) displaying the Inferior field wherein the Central field is excluded; and, FIG. 2 shows a schematic diagram of the basic system components forming an apparatus for assessing the presence of glaucomatous damage, in accordance with the present invention.

DESCRIPTION OF THE PREFERRED EMBODIMENTS

Figure 2:
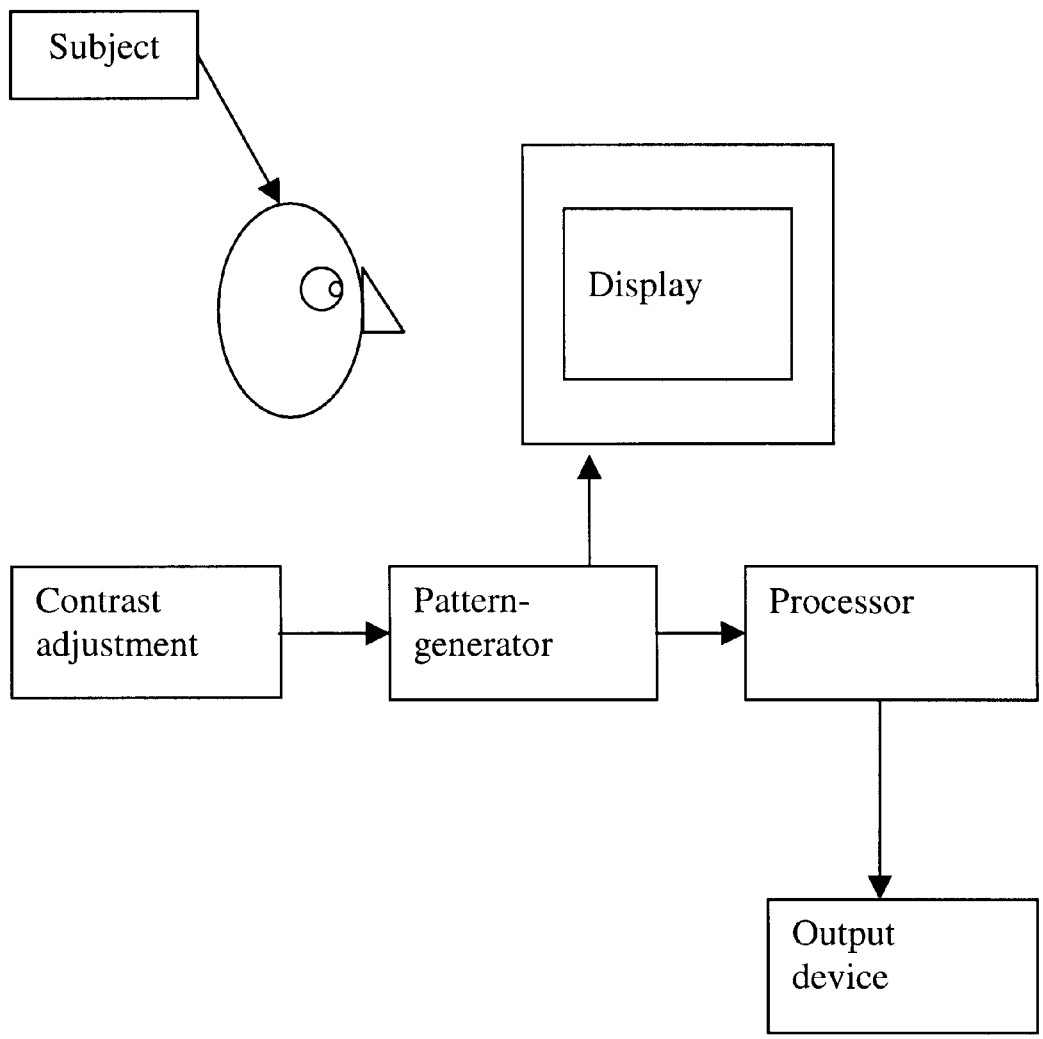

As noted in the specifications of Australian patent No 611,585 and U.S. Pat. No. 5,065,767, in 1966, D H Kelly, in his paper entitled "Frequency doubling in visual responses" (which was published in the *Journal of the Optical Society of America*, Volume 56, page 1628, 1966), reported that when sinusoidal grating patterns with spatial frequencies below a few cycles per degree are modulated so that the contrast between the bars or striations of the pattern is varied at rates higher than 10 Hz, the gratings appear as spatial frequency-doubled sinusoids to persons of normal vision. D H Kelly's subsequent work (reported in his paper entitled "Nonlinear visual responses to flickering sinusoidal gratings", which was published in the *Journal of the Optical Society of America*, Volume 71, page 1051, 1981) has shown that this second-harmonic distortion of the human visual response is due to the optical pathway between the eye and the brain having both a linear component and a non-linear component.

The retinal ganglion cells of higher primates, including humans, are known to be of two dominant types, namely "M" type ganglion cells and "P" type ganglion cells, each of which respond to visual stimuli. However, the P type ganglion cells respond in a sluggish manner and do not contribute to the production of the images with which the present invention is concerned. The M type cells consist of "y-type" ganglion cells (usually designated "$M_y$" cells) and "x-type" ganglion cells (usually designated "$M_x$" cells). There are significantly fewer $M_y$ cells than $M_x$ cells. Recent work has shown that the $M_y$ cells are responsible for the non-linear component of the optical pathway, while the $M_x$ cells primarily respond in a linear fashion.

Recent experimental work with primates has shown that the retinal ganglion cells are killed at the onset of glaucoma in proportion to their size (see the paper by Y Glovinsky et al, entitled "Chronic glaucoma damages large optic nerve fibres", which was published in *Investigative Ophthalmology and Visual Science*, Volume 32, page 484, 1991). At the same time, three single cell electrophysiological studies have indicated that $M_y$ cells are larger than $M_x$ cells by virtue of their larger receptive field size and more rapid conduction velocities (see the papers by (i) E Kaplan and R M Shapley, entitled "X and y cells in the lateral geniculate nucleus of macaque monkeys", which was published in *Journal of Physiology*, Volume 330, page 125, 1982; (ii) R T Marrocco et al, entitled "Spatial summation and conduction latency classification of cells of the lateral geniculate nucleus of macaques", which was published in *Journal of Neuroscience*, Volume 2, 1275, 1982; and (iii) C Blakemore and F Vital-Duran, entitled "Organisation and post-natal development of the monkey's lateral geniculate nucleus", which was published in *Journal of Physiology*, Volume 380, page 453, 1986). Since $M_y$ cells are the largest of the retinal ganglion cells, it would appear that these will be amongst the first cells killed when a person contracts the disease glaucoma.

Another factor which makes examination of $M_y$ cell function attractive from the point of glaucoma diagnosis is that the coverage factor of $M_y$ cells is very, low (see the paper by Crook et al, entitled "Visual resolution of macaque retinal ganglion cells", which was published in *Journal of Physiology*, Volume 396, page 205, 1988), indicating that the loss of even a single cell will lead to a distinct scotoma in the lattice of $M_y$ cell receptive fields.

A further observation which makes the frequency-doubled illusion and $M_y$ cells interesting from the perspective of glaucoma diagnosis is that other neurological disorders which commonly produce visual deficits do not affect vision in the spatiotemporal region requisite for seeing the frequency doubled illusion. For example, amblyopia (see the paper by R F Hess et al, entitled "On the relationship between pattern and movement perception in strabismic amblyopia", which was published in *Vision Research*, Volume 18, page 375, 1978), optic neuritis (see the papers by (i) R F Hess and G Plant, entitled "The effect of temporal frequency variation on the threshold contrast sensitivity deficits in optic neuritis", which was published in *Journal of Neurology, Neurosurgery and Psychiatry*, Volume 46, page 322, 1983; and (ii) G K Edgar et al, entitled "Optic neuritis, variations in temporal modulation sensitivity with retinal eccentricity", which was published in *Brain*, Volume 113, page 487, 1990) and Parkinson's disease (see the paper by Marx et al, entitled "Temporal frequency-dependent VEP changes in Parkinson's disease", which was published in *Vision Research*, Volume 26, page 185, 1986) do not appear to affect perception of rapidly flickered coarse patterns. Thus, stimuli tailored to the production of the frequency-doubled illusion may stimulate a visual pathway highly sensitive to glaucomatous damage and the results of any test for glaucoma based on such stimuli should be little affected by other neurological disorders affecting vision. Indeed, testing of subjects using the method described in the specification of Australian Patent No 611,585 and in the specification of the corresponding U.S. Pat. No. 5,065,767 has shown that a deficit in the ability of a subject to see the frequency-doubled illusion is highly correlated with glaucomatous damage.

Pattern electroretinogram (PERG) studies have shown that the frequency-doubled illusion arises in the retina rather than at a more central level. In several recent PERG studies, investigators adjusted the spatial scale and temporal modulation frequency of their visual stimuli in an attempt to find stimulus conditions which better discriminate glaucomatous and normal eyes (see, for example, the paper by M A Johnson et al, entitled "Pattern-evoked potentials and optic nerve fibre loss in monocular laser-induced glaucoma", which was published in *Investigative Ophthalmology and Visual Science*, Volume 30, page 897, 1989). Although not encompassing the region where the frequency-doubled illusion is strongest, these workers have shown that as the stimulus conditions approach those which result in the frequency-doubled illusion (that is, low spatial frequencies and high temporal frequencies), the ability to discriminate glaucomatous eyes is enhanced. Thus it would appear that stimuli designed to maximally evoke the frequency-doubled illusion from each part of the retina should enhance the value of psychophysical testing for glaucomatous damage.

In the light of this work, and the earlier establishment that (a) the visibility of the spatial frequency-doubled illusion described by D H Kelly is affected by the presence of glaucoma; and (b) the disturbance of the visibility of the frequency-doubled illusion visual response is exhibited at an early stage of glaucoma—well before the loss of ganglion cells is sufficient to produce a scotoma; the present inventor hypothesised that (c) since glaucomatous scotomas often assume an arcuate appearance, circling primarily the superior or the inferior peripheral visual field, these areas should be tested separately and together;

(d) thresholds for the observation of the frequency-doubled illusion, determined from similar regions in the visual field of a subject (such as the Inferior and Superior halves of the visual field) should be ranked, and the ranked thresholds should be used for a discriminant analysis since glaucoma can cause damage in any such region independently; and (e) the different visual response for the regions of the visual field should not be exhibited by persons suffering from amblyopia, optic neuritis or Parkinson's disease.

Thus if use of the frequency-doubled illusion is combined with a method which allows measurement of the response to these stimuli in each region of the visual field, better detection of early glaucomatous damage can be expected. This, of course, is the basis for the present invention.

The implementation of the present invention to which the accompanying drawing (FIGS. 1(*a–d*) is relevant involves finding the contrast threshold for seeing the frequency-doubled effect in the four regions or zones of the visual field or space that are shown in the drawing. In each zone, a coarse sinusoidal grating, with its contrast modulated at 25+15 Hz, is presented to a subject and the threshold values of the contrast, at which the frequency-doubled illusion is just visible to the subject, is determined. The thresholds for each zone are determined sequentially. In each case a fixation spot is presented in the visual field or space, centered on the point 0° azimuth and 0° elevation. The present inventor has termed the four zones in which the pattern is presented (i) the Whole Field (top left of the drawing, FIG. 1(*a*)), (ii) Central (bottom left of the drawing, FIG. 1(*c*)), (iii) Superior (top right of the drawing, FIG. 1(*b*)), and (iv) Inferior (bottom right of the drawing, FIG. 1(*d*)).

Now the contrast (C) of the sinusoidal grating patterns is defined as:

$$C=(I_{max}-I_{min})/(I_{max}+I_{min}) \tag{1}$$

where $I_{max}$ and $I_{min}$ refer to the maximum and minimum intensities in the stimulus waveform. The waveforms are sinusoidal gratings whose contrast is reversed, which can be described by the function:

$$W(x,t)=I(1+CH(t) \cos (2\pi f x+\phi)) \tag{2}$$

where I is the main luminance which should be 40 to 50 nits, C is the contrast, ranging from 0 to 1, H(t) is a square wave alternating from −1 to 1 at about 25 Hz, f is the spatial frequency, and $\phi$ is a spatial phase shift. In principle, H(t)

could also be a sinusoid in time. The masking of the patterns into the regions displayed in the drawing is effected in a manner such that any part of the visual display which is not covered by the test pattern is held at the mean luminance of the test pattern. In the "Central" stimulus zone, the spatial frequency is 0.5 cycles per degree while in the other three presentation zones in the visual field of the subject, it is 0.25 cycles per degree.

These spatial frequency values were experimentally determined to be near optimal, and were used in the demonstration of the method presented below. In practice, the spatial frequency of the pattern used in the central zone should be in the range 0.2 to 2.0 cycles per degree and the spatial frequency of the whole field and peripheral zones, such as the superior and inferior zones could be in the range 0.1 to 0.5 cycles per degree.

During the establishment of the four threshold contrast values, either the subject or the operator controls the contrast (C) of the images. At the outset of each test, a subject is presented with the pattern at the maximum contrast. The contrast is then lowered to a point where the subject just begins to see the presence of the pattern of thick vertical stripes when the frequency-doubled illusion is visible. Fine adjustments of the contrast are then made until the subject indicates that the contrast is at a value where the subject can only just discern the thick vertical stripes of the test pattern.

Two or more repeats of each threshold determination should be undertaken, and the average value of the threshold contrasts should be used in the evaluation of the presence of glaucomatous damage to the subject's retina.

Setting the contrast to the maximum at the outset of each threshold contrast determination serves to remind the subject of the nature of the test pattern. It also puts the subject at ease in the sense that the subject is reassured that something can be seen. The latter consideration breaks down for some subjects who have glaucoma at an advanced stage. Those subjects may report seeing nothing on the CRT tube used to present the sinusoidal patterns, even at a contrast of 1 (i.e., 100 per cent).

The contrast thresholds obtained are heteroskadastic (that is, the variance scales with the mean). Accordingly, it is necessary to work with logarithmic units of contrast. To demonstrate the power of the new method an analysis was employed in which only thresholds from the superior and inferior hemifields of subjects was first sorted according to which of the two hemifield tests required the highest contrast for a subject to see the frequency doubled illusion in that hemifield, the higher contrast threshold being referred to as the worst hemifield threshold. Data was obtained in a study with an initial cohort of 43 normals and 31 Primary Open Angle Glaucoma patients who returned for up to 7 repeated threshold tests at intervals of approximately 4 months. These 4 monthly tests will be referred to as "visits". In these tests the contrasts, as defined in equation 1, of the frequency doubled test stimuli was defined on a scale from 0 to 127, where 0 indicates a contrast of 0 and 127 indicates a maximal contrast of 1. Examination of the worst hemifield thresholds showed that the probability of a given eye having glaucoma was given by equation 3, where T is the mean of the natural logarithm of the contrast of the worst hemifield threshold, and where contrast is on the aforementioned scale from 0 to 127.

$$p = exp(-11.076 + 4.484*T)/(1 + exp(-11.076 + 4.484*T)) \quad (3)$$

Where values of p greater than 0.5 are taken to indicate glaucoma in a given eye. On this basis the sensitivities and specificities for the left and right eyes of the normal and glaucoma subjects were as shown in Table 1 for the first 7 test visits. The sensitivities and specificities presented assume a prior probability of encountering a subject with glaucoma of 50%.

TABLE 1

| Visit Number | | Right eye | Left eye |
| --- | --- | --- | --- |
| 1 | Sens | 0.92 | 0.84 |
|   | Spec | 0.83 | 0.83 |
| 2 | Sens | 0.88 | 0.88 |
|   | Spec | 0.82 | 0.84 |
| 3 | Sens | 0.83 | 0.89 |
|   | Spec | 0.88 | 0.88 |
| 4 | Sens | 0.81 | 0.80 |
|   | Spec | 0.92 | 0.95 |
| 5 | Sens | 0.81 | 0.80 |
|   | Spec | 0.92 | 0.95 |
| 6 | Sens | 0.91 | 0.79 |
|   | Spec | 0.93 | 0.93 |
| 7 | Sens | 0.74 | 0.84 |
|   | Spec | 0.75 | 0.81 |
|   | Means Sens | 0.86 | 0.83 |
|   | Means Spec | 0.88 | 0.90 |

The mean sensitivity for both eyes was 0.85 and the mean specificity 0.89 which is as good or better than figures published for automated perimetry. The principle advantage of this method being that if only the superior and inferior hemifield thresholds need to be determined then the whole test procedure for the two eyes requires somewhat less than 4 minutes for both eyes. Sensitivities and specificities obtained when thresholds obtained for all 4 stimuli depicted in FIG. 1 were a few percent higher than those shown in Table 1. Other data, such as optic disc cupping and intraocular tension, can be included with the thresholds in the discriminant analysis to increase the sensitivity and specificity of the present invention.

It will be appreciated that the present invention involves determining a threshold value by a "method of adjustment" (MOA) procedure. There has been much discussion among experimenters of algorithms for determining thresholds.

When tested head to head, however, the performance of various schemes including MOA do not differ greatly (see the paper by A Hesse, entitled "Comparison of several psychophysical procedures with respect to threshold estimates, reproducibility and efficiency", which was published in *Acustica*, Volume 59, page 265, 1986). It is known that adaptive algorithms suffer tremendously with naive subjects (see the paper by Stillman, entitled "A comparison of three adaptive psychophysical procedures using inexperienced listeners", which was published in *Perception and Psychophysics*, Volume 46, page 345, 1989). It seems clear that factors ranging from subject trepidation to flippancy can generate erroneous responses from naive subjects, and those responses play havoc with adaptive estimation algorithms. Thus, in practice, the threshold estimation is neither quicker nor more accurate when adaptive algorithms are used. Many automated methods also produce significant bias without large numbers of repeats (see the paper by Simpson, entitled "The step method: a new adaptive psychophysical procedure", which was published in *Perception and Psychophysics* Volume 45, page 572, 1989). In addition, adaptive schemes often make assumptions about the shape of the psychometric function, which appears to be quite variable in sufferers of glaucoma (see the paper by Chauhan et al, entitled "Characteristics of frequency-of-seeing curves in normal subjects, patients with suspected glaucoma, and patients with glaucoma", which was published in *Investigative Ophthalmology and Visual Science*, Volume 34, page 3534, 1993). One thing that is clear is that in the present invention, the MOA procedure is quick yet reasonably accurate. Thus, although more accurate threshold determination schemes may be devised in the future, it appears that with the rapid method of the present invention, the best results for any psychophysical test to date have been achieved.

It will be appreciated that only one method and apparatus for the present invention has been described, by way of example, with reference to the accompanying drawing, and that variations and modifications to this method will be understood to persons skilled in the art. All such variations and modifications should be considered to fall within the scope of the invention as hereinbefore described and as hereinafter claimed.

I claim:

1. A method of assessing the presence of any glaucomatous damage to the visual system of a subject comprising the steps of:
   (a) dividing the visual field of view of said subject into a plurality of zones;
   (b) presenting patterns within each of said zones, said patterns having spatial and temporal characteristics consistent with observing a spatial frequency doubled illusion;
   (c) measuring a contrast threshold at which said subject can just discern a spatial frequency doubled illusion pattern in each of said zones; and,
   (d) comparing said contrast thresholds with each other and with standard values for normal vision to determine the presence of any glaucomatous damage.

2. The method of claim 1 wherein said zones are presented to said subject on a cathode ray tube.

3. The method of claim 1, wherein said zones comprise a whole visual field, a superior visual field, an inferior visual field and a central visual field.

4. The method of claim 1, wherein said contrast thresholds are determined by a plurality of iterations for each zone.

5. The method of claim 1, wherein said patterns comprise sinusoidal grating patterns having generally elongate striations being modulated at a frequency in the range of 10 Hz to 50 Hz.

6. An apparatus for assessing the presence of glaucomatous damage to the visual system of a subject, comprising:
   a display system adapted to present patterns in a plurality of zones within the visual field of a subject, said patterns having spatial and temporal characteristics consistent with observing a spatial frequency double illusion; and
   means to adjust the contrast of said patterns to a contrast threshold at which said subject can just discern each said spatial frequency doubled illusion pattern.

7. The apparatus of claim 6, further comprising:
   means to calculate the mean of the logarithm of the threshold values to determine the zone which produces the highest threshold; and
   means to compare said maximal threshold with a standard value based on subjects having normal vision.

8. The apparatus of claim 6, wherein said plurality of presented zones include a whole visual field, a superior visual field, an inferior visual field and a central visual field.

9. The apparatus of claim 8 wherein the spatial frequency of the patterns used in the central visual field is in the range of 0.2 to 2.0 cycles per degree and the spatial frequency in the whole visual field, superior visual field and inferior visual field is in the range of 0.1 to 0.5 cycles per degree.

10. The apparatus of claim 6, wherein said displaying system presents sinusoidal grating patterns having generally elongate striations modulated at a frequency in the range of 10 Hz to 50 Hz.

11. The apparatus of claim 6, wherein said display system is a cathode ray tube screen.

12. The apparatus of claim 6, wherein the means to adjust the contrast has a resolution of about 1 part in 1024 parts, and wherein the contrast is presented in logarithmic units with incremental steps of about 0.5 decibels beginning at a lowest contrast of about −44 decibels, which corresponds to a minimum contrast of about 0.006.

* * * * *